(12) United States Patent
Benson et al.

(10) Patent No.: US 7,402,678 B2
(45) Date of Patent: Jul. 22, 2008

(54) MULTIFUNCTIONAL AMINE CAPTURE AGENTS

(75) Inventors: Karl E. Benson, St. Paul, MN (US); Cary A. Kipke, Woodbury, MN (US); Brinda B. Lakshmi, Woodbury, MN (US); Charles M. Leir, Falcon Heights, MN (US); George G. I. Moore, Afton, MN (US); Rahul Shah, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 537 days.

(21) Appl. No.: 11/015,543

(22) Filed: Dec. 17, 2004

(65) Prior Publication Data

US 2006/0135783 A1    Jun. 22, 2006

(51) Int. Cl.
*C07D 275/02* (2006.01)
(52) U.S. Cl. ................. 548/213; 548/436; 548/475; 548/546
(58) Field of Classification Search ................. 548/213, 548/436, 546
See application file for complete search history.

(56) References Cited

U.S. PATENT DOCUMENTS

| | | | |
|---|---|---|---|
| 3,442,815 A | 5/1969 | Rauhut et al. | |
| 3,801,533 A | 4/1974 | Tetenbaum et al. | |
| 4,233,029 A | 11/1980 | Columbus | |
| 5,583,114 A | 12/1996 | Barrows et al. | |
| 5,587,513 A | 12/1996 | Pohmer et al. | |
| 5,674,742 A | 10/1997 | Northrup et al. | |
| 5,700,612 A | 12/1997 | Kato et al. | |
| 5,874,500 A | 2/1999 | Rhee et al. | |
| 6,156,270 A | 12/2000 | Buechler | |
| 6,369,893 B1 | 4/2002 | Christel et al. | |
| 6,573,338 B2 | 6/2003 | Halverson et al. | |
| 6,656,428 B1 | 12/2003 | Bickoff et al. | |
| 7,169,933 B2 * | 1/2007 | Benson et al. ............. 548/207 |
| 2003/0170474 A1 | 9/2003 | Qiao et al. | |
| 2003/0170881 A1 | 9/2003 | Davis et al. | |

FOREIGN PATENT DOCUMENTS

| | | |
|---|---|---|
| CA | 2 369 720 | 7/2003 |
| EP | 0 010 844 | 5/1980 |
| EP | 0 177 740 | 5/1986 |
| EP | 0 446 047 | 9/1992 |
| EP | 0 535 236 | 4/1993 |
| EP | 0 657 737 | 6/1995 |
| EP | 0 814 381 | 12/1997 |
| JP | 1-114861 | 8/1989 |
| JP | 03055544 | 3/1991 |
| JP | 5-188663 | 7/1993 |
| JP | 9-54463 | 2/1997 |
| JP | 11-109630 | 4/1999 |
| JP | 2003-322860 | 11/2003 |
| WO | WO 00/16903 | 2/2000 |
| WO | WO 01/23892 | 4/2001 |
| WO | WO 02/088296 | 11/2002 |
| WO | WO 02/095940 | 11/2002 |
| WO | WO 03/068712 | 8/2003 |
| WO | WO 2004/067732 | 8/2004 |

OTHER PUBLICATIONS

Benson et al., Acousto-Mechanical Detection Systems and Methods of Use, U.S. Appl. No. 60/533,169, filed Dec. 30, 2003.
Tseng et al., J.Org. Chem., vol. 44, No. 23, 1979, pp. 4113-4116 XP-002331678.
Adams et al., Journal of American Chemical Society, 78, 3825-3828, 1956, XP-002331677.
Mustafa et al, Journal of American Chemical Society, 79, 1945-1949, 1957, XP-002331676.
Guo et al., Journal of Fluorine Chemistry, 52, 29-36, 1991, XP-002331675.
Yoshio et al., Database accession No. 1979: 492034 XP-002331680.
Toshiaki et al, Database accession No. 1995: 708887 XP-002331681.
Satoshi et al., Database accession No. 2004: 1125476 XP-00231679.
Grate et al., "Acoustic Wave Sensors" vol. 2, pp. 38-83, 1996 (XP002334970).

* cited by examiner

*Primary Examiner*—Kamal A Saeed
(74) *Attorney, Agent, or Firm*—Jean A. Lown; Ann M. Mueting

(57) ABSTRACT

Multifunctional compounds having acylsulfonamide amine-reactive groups are described that can be used for the capture of amine containing materials.

18 Claims, No Drawings

MULTIFUNCTIONAL AMINE CAPTURE AGENTS

GOVERNMENT RIGHTS

This invention was made with Government support under Contract No. DAAD13-03-03-C-0047 awarded by the U.S. Army. The Government has certain rights in this invention.

BACKGROUND

Amine-containing materials, such as amine-containing analytes, amino acids, DNA fragments, RNA fragments, protein fragments, organelles, and immunoglobins, immobilized on the surface of a substrate can be used in numerous applications. The covalent attachment of amine-containing materials to a substrate can be accomplished, for example, by the reaction of the amine with a reactive group on the surface of the substrate. This amine-reactive functional group can be, for example, an activated acyl derivative, such as an N-hydroxy succinimide ester; or, an active cyclic acyl compound, such as azlactone. A stable amide bond is formed from reaction of the amine with the active acyl group, either with expulsion of N-hydroxy succinimide or opening of the azlactone.

Although a wide variety of amine-reactive compounds of the type described above, with an amine capturing functional group on one end and a different substrate anchoring functional group on the other end of a divalent linking group, can be conveniently synthesized, many such modifications require difficult separations to achieve the necessary selectively substituted compound. For example, longer or oligomeric divalent linking groups, or, especially, branched or multi-functional linking groups, would be difficult to prepare having a single, substrate specific, reactive functional group on only one end of the molecule. An alternative approach involves converting some or all functional groups to amine capture functional groups. Such molecules could be beneficial for efficient attachment, as well as for control of the activity of the immobilized amine-containing material, especially in biological systems.

Additionally, some surfaces may have few or no complementary functional groups for anchoring amine compounds. Such inert surfaces are often conveniently functionalized by treatment with a surface aminating agent, such as amino alkyl silanes or polyethylene imine. Subsequent exposure of these aminated surfaces to solutions of excess di- or multi-functional amine-capture compounds would convert the surface of the substrate into a surface with grafts of amine-reactive functional groups.

Thus, there exists a need for compounds for reaction with amine-functional surfaces having di- and multi-functional amine-reactive, terminal functional groups.

SUMMARY

The present invention provides multi-functional compounds with terminal acyl sulfonamide groups. These compounds can be used to treat amine-functional surfaces. Such compounds can also be used as crosslinkers for amine containing materials to provide gels and hydrogels, for example.

The compounds are of the formula:

(A-)$_y$-Q wherein A is independently selected from the group consisting of functional groups having the following formulas:

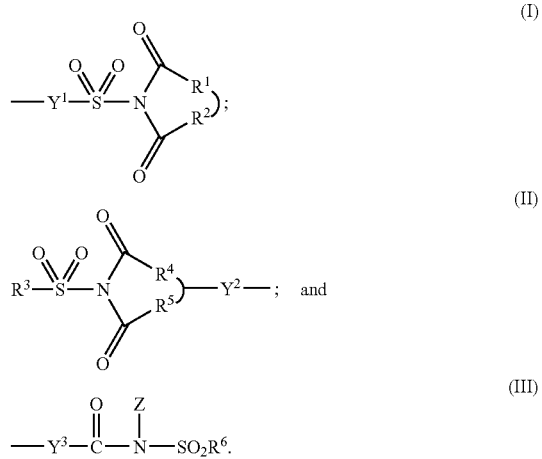

wherein $R^1$, $R^2$, $R^3$, $R^4$, $R^5$, $R^6$, $Y^1$, $Y^2$, $Y^3$, y, Q, and Z are defined herein below, with the proviso that Q, $Y^1$, $Y^2$, and $Y^3$ are free of disulfide groups.

Definitions

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "alkyl" refers to a monovalent radical of an alkane and includes groups that are linear, branched, cyclic, or combinations thereof. The alkyl group typically has 1 to 30 carbon atoms. In some embodiments, the alkyl group contains 1 to 20 carbon atoms, 1 to 10 carbon atoms, 1 to 6 carbon atoms, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

As used herein, the term "alkylene" refers to a divalent radical of an alkane. The alkylene can be straight-chained, branched, cyclic, or combinations thereof. The alkylene typically has 1 to 200 carbon atoms. In some embodiments, the alkylene contains 1 to 100, 1 to 80, 1 to 50, 1 to 30, 1 to 20, 1 to 10, 1 to 6, or 1 to 4 carbon atoms. The radical centers of the alkylene can be on the same carbon atom (i.e., an alkylidene) or on different carbon atoms.

As used herein, the term "aralkyl" refers to a monovalent radical of the compound Ar—R where Ar is an aromatic carbocyclic group and R is an alkyl group.

As used herein, the term "aralkylene" refers to a divalent radical of formula —R—Ar— where Ar is an arylene group and R is an alkylene group.

As used herein, the term "aryl" refers to a monovalent aromatic carbocyclic radical. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "arylene" refers to a divalent radical of a carbocyclic aromatic compound having one to five rings that are connected, fused, or combinations thereof. In some embodiments, the arylene group has up to 5 rings, up to 4 rings, up to 3 rings, up to 2 rings, or one aromatic ring. For example, the arylene group can be phenylene.

The above aryl and arylenes can optionally contain substituents such as lower alkyl, halo, and alkoxy.

As used herein, the term "carbonyl" refers to a divalent group of formula —(CO)—.

As used herein, the term "carbonylimino" refers to a divalent group of formula —(CO)NR$^a$— where R$^a$ is hydrogen, alkyl, or aryl.

As used herein, the term "carbonyloxy" refers to a divalent group of formula —(CO)—.

As used herein, the term "chloroalkyl" refers to an alkyl having at least one hydrogen atom replaced with a chlorine atom.

As used herein, the term "disulfide" refers to a divalent group of formula —S—S—.

As used herein, the term "fluoroalkyl" refers to an alkyl having at least one hydrogen atom replaced with a fluorine atom. Some fluoroalkyl groups are perfluoroalkyl groups.

As used herein, the term "heteroalkylene" refers to a divalent alkylene having one or more carbon atoms replaced with a sulfur, oxygen, or NR$^d$ where R$^d$ is hydrogen or alkyl. The heteroalkylene can be linear, branched, cyclic, or combinations thereof and can include up to 400 carbon atoms and up to 30 heteroatoms. In some embodiments, the heteroalkylene includes up to 300 carbon atoms, up to 200 carbon atoms, up to 100 carbon atoms, up to 50 carbon atoms, up to 30 carbon atoms, up to 20 carbon atoms, or up to 10 carbon atoms.

As used herein, the term "heteroarylene" refers to a divalent arylene having one or more carbon atoms replaced with a sulfur, oxygen, or NR$^f$ where R$^f$ is hydrogen or alkyl.

As used herein, the term "oxy" refers to a divalent group of formula —O—.

As used herein, the term "perfluoroalkyl" refers to an alkyl group in which all of the hydrogen atoms are replaced with fluorine atoms.

As used herein, the term "thio" refers to a group of formula —S—.

As used herein, the term "room temperature" refers to a temperature of about 20° C. to about 25° C. or about 22° C. to about 25° C.

As used herein, a curve connecting two groups in a formula indicates that the two groups together form part of a cyclic structure.

For any of the compounds presented herein, each one of the following variables (e.g., R$^1$, R$^2$, Y$^1$, Y$^2$, Z, A, and so on) in any of its embodiments can be combined with any one or more of the other variables in any of their embodiments as would be understood by one of skill in the art. Each of the resulting combinations of variables is an embodiment of the present invention.

When a group (or substituent or variable) is present more than once in a compound or polymer described herein, each group (or substituent or variable) is independently selected, whether explicitly stated or not. For example, for the formula (A)$_y$-Q each A group is independently selected. Furthermore, when more than one A group is present and each A group contains one or more L groups, as defined below, then each L group is also independently selected.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention provides compounds of the formula:

(A-)$_y$-Q wherein each A is independently selected from the group consisting of functional groups having the following formulas:

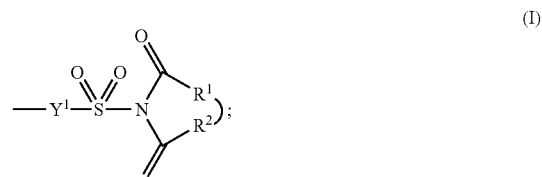

(I)

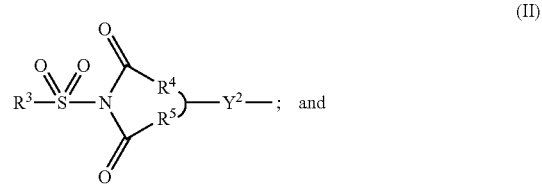

(II)

(III)

wherein R$^1$, R$^2$, R$^3$, R$^4$, R$^5$, R$^6$, Y$^1$, Y$^2$, Y$^3$, y, Q, and Z are defined herein below, with the proviso that Q, Y$^1$, Y$^2$, and Y$^3$ are free of disulfide groups. Such A groups are preferably terminal groups.

Herein, in the compounds of the formula (A-)$_y$-Q, Q is a single bond or a y-valent atom or group. In certain embodiments, Q is an atom selected from C, N, S, O, or P. In certain embodiments, Q is a y-valent group containing up to 20 carbon atoms and up to 6 heteroatoms and/or functional groups (such as carbonyl groups). In certain embodiments, Q includes a ring system. Exemplary Q groups include carbonyl, alkylenes, alkanetriyl (i.e., a trivalent radical of an alkane), heteroalkylenes, arylenes, heteroarylenes, alkyleneoxy-alkylenes (e.g., —CHCH$_2$OCH$_2$CH—), alkylene-carbonyl-alkylenes, and combinations thereof (e.g., groups including both alkylene and arylene groups with or without heteroatoms and/or functional groups). Exemplary Q ring structures include the following:

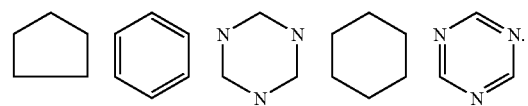

Herein, y is an integer of 2 to 10. In certain embodiments, y is an integer of 2 to 6. In some embodiments, y is an integer of 2 to 4. In some embodiments, y is an integer of 2 to 3. In some embodiments, y is 2 and the A groups are terminal.

The A groups may be the same or different. For synthetic convenience, however, they are often the same.

Herein, in Formula I, $R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group.

Herein, in Formula II, $R^3$ is an alkyl, aryl, aralkyl, or —$NR^aR^b$ wherein $R^a$ and $R^b$ are each an alkyl group or taken together with the nitrogen atom to which they are attached form a four to eight membered heterocyclic group.

In certain embodiments of Formula II, $R^3$ is an alkyl, aryl, or aralkyl group. Suitable alkyl groups typically contain no greater than 30 carbon atoms, no greater than 20 carbon atoms, no greater than 10 carbon atoms, no greater than 6 carbon atoms, or no greater than 4 carbon atoms. In some compounds, the alkyl group is methyl, ethyl, or propyl. Suitable aryl groups typically contain 6 to 18 carbon atoms, 6 to 12 carbon atoms, or 6 carbon atoms. In some compounds, the aryl group is phenyl. An example of an aryl group is 4-methylphenyl. Suitable aralkyl groups typically contain an aryl group having 6 to 30 carbon atoms and an alkyl group having no greater than 30 carbon atoms.

In other embodiments of Formula II, $R^3$ is a group —$NR^aR^b$ where $R^a$ and $R^b$ are alkyl groups having no greater than 10 carbon atoms, no greater than 6 carbon atoms, or no greater than 4 carbon atoms. Alternatively, the $R^1$ and $R^b$ groups can combine together with the nitrogen atom to which they are attached to form a 4 to 8 membered ring structure. For example, $R^a$ and $R^b$ can combine to form a five or six membered heterocyclic group having a nitrogen heteroatom.

Herein, in Formula II, $R^4$ and $R^5$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group.

Herein, in Formula III, $R^6$ is an alkyl, fluoroalkyl, chloroalkyl, aryl, —$NR^cR^d$ wherein $R^c$ and $R^d$ are each an alkyl group or taken together with the nitrogen atom to which they are attached form a four to eight membered cyclic group, or $R^6$ taken together with $R^e$ and the groups to which they are attached form the four to eight membered heterocyclic or heterobicyclic group that can be fused to the optional aromatic group, optional saturated or unsaturated cyclic group, or optional saturated or unsaturated bicyclic group.

In some embodiments of Formula III, $R^6$ can be a $C_{1-30}$ alkyl, a $C_{1-10}$ alkyl, or a $C_{1-6}$ alkyl. In other embodiments of Formula III, $R^6$ can be a $C_{1-30}$ fluoroalkyl, a $C_{1-10}$ fluoroalkyl, or a $C_{1-4}$ perfluoroalkyl group. In still other embodiments of Formula III, $R^6$ can be a $C_{6-12}$ aryl. For example $R^6$ can be a phenyl group.

Herein, Z is an alkyl, aryl, or —$(CO)R^e$. In some embodiments of Formula III, Z can be alkyl or aryl. For example, Z can be a $C_{1-6}$ alkyl. In other examples, Z can be a $C_{6-12}$ aryl. In other embodiments of Formula I, Z can be a —$(CO)R^e$ group, wherein $R^e$ together with $R^6$ and groups to which they are attached form a four to eight membered heterocyclic or heterobicyclic group having a nitrogen heteroatom and a sulfur heteroatom, wherein the heterocyclic or heterobicyclic group can be fused to an optional aromatic group, optional saturated or unsaturated cyclic group, or optional saturated or unsaturated bicyclic group.

Herein, $Y^1$, $Y^2$, and $Y^3$ are each independently a single bond or a divalent group selected from the group consisting of an alkylene, heteroalkylene, arylene, heteroarylene, carbonyl, carbonyloxy, carbonylimino, oxy, thio, —$NR^f$— where $R^f$ is hydrogen or alkyl, and combinations thereof. In certain embodiments, $Y^1$, $Y^2$, and $Y^3$ are each independently selected from the group consisting of groups having the following formulas —$Y^{1a}$—$Ar^1$— and —$Ar^1$—$Y^{1a}$—, wherein: $Ar^1$ is an arylene; and $Y^{1a}$ is selected from the group consisting of a single bond, alkylene, heteroalkylene, carbonyl, carbonyloxy, carbonylimino, oxy, thio, —$NR^f$— where $R^f$ is hydrogen or alkyl, and combinations thereof.

In certain embodiments, $Y^1$, $Y^2$, and $Y^3$ are each independently selected from the group consisting of groups having the following formulas: —$Y^{1a}$—$Ar^1$— and —$Ar^1$—$Y^{1a}$—. In such formulas, $Ar^1$ is an arylene (preferably, a phenylene), and $Y^{1a}$ is selected from the group consisting of a single bond, alkylene, heteroalkylene, carbonyl, carbonyloxy, carbonylimino, oxy, thio, —$NR^f$— where $R^f$ is hydrogen or alkyl, and combinations thereof.

In certain embodiments, $Y^1$, $Y^2$, and $Y^3$ each independently includes a first alkylene group linked to an arylene group with a group selected from the group consisting of a carbonyl, carbonyloxy, carbonylimino, oxy, thio, —$NR^f$— where $R^f$ is hydrogen or alkyl, and combinations thereof. In certain of these embodiments, the first alkylene group is further linked to a second alkylene or a first heteroalkylene group with a group selected from the group consisting of a carbonyl, carbonyloxy, carbonylimino, oxy, thio, —$NR^f$— where $R^f$ is hydrogen or alkyl, and combinations thereof. In certain of these embodiments, additional alkylene or heteroalkylene groups can be linked to the second alkylene or to the first heteroalkylene group with a group selected from the group consisting of a carbonyl, carbonyloxy, carbonylimino, oxy, thio, —$NR^f$— where $R^f$ is hydrogen or alkyl, and combinations thereof.

In certain embodiments, $Y^1$, $Y^2$, and $Y^3$ each independently includes a first heteroalkylene group linked to an arylene with a group selected from the group consisting of a carbonyl, carbonyloxy, carbonylimino, oxy, thio, —$NR^f$— where $R^f$ is hydrogen or alkyl, and combinations thereof. In certain of these embodiments, the first heteroalkylene group is further linked to a second heteroalkylene or to a first alkylene group with a group selected from the group consisting of a carbonyl, carbonyloxy, carbonylimino oxy, thio, —$NR^f$— where $R^f$ is hydrogen or alkyl, and combinations thereof. In certain of these embodiments, additional alkylene or heteroalkylene groups linked to the second heteroalkylene or to the first alkylene group with groups selected from the group consisting of carbonyl, carbonyloxy, carbonylimino group, oxy, thio, —$NR^f$— where $R^f$ is hydrogen or alkyl, and combinations thereof.

In certain embodiments, $Y^1$, $Y^2$, and $Y^3$ each independently includes a first alkylene group connected to a second alkylene group or to a first heteroalkylene group with a group selected from the group consisting of a carbonyl, carbonylimino, carbonyloxy, oxy, thio, —$NR^f$— where $R^f$ is hydrogen or alkyl, and combinations thereof. In certain of these embodiments, additional alkylene or heteroalkylene groups connected to the second alkylene group or the first heteroalkylene group with a group selected from the group consisting of a carbonyl, carbonylimino, carbonyloxy, oxy, thio, —$NR^f$— where $R^f$ is hydrogen or alkyl, and combinations thereof.

In certain embodiments, $Y^1$, $Y^2$, and $Y^3$ each independently includes a first heteroalkylene group connected to a second heteroalkylene group or to a first alkylene group with a group selected from the group consisting of a carbonyl, carbonylimino, carbonyloxy, oxy, thio, —$NR^f$— where $R^f$ is hydrogen or alkyl, and combinations thereof. In certain of these embodiments, additional alkylene or heteroalkylene groups connected to the second heteroalkylene group or the first alkylene group.

In certain embodiments, $Y^1$, $Y^2$, and $Y^3$ are each independently a heteroalkylene having, for example, 1-30 carbon atoms and up to 30 heteroatoms selected from the group consisting of N, O, S, and combinations thereof, wherein the heteroalkylene group is linear, branched, cyclic, or combinations thereof.

In certain embodiments, $Y^1$, $Y^2$, and $Y^3$ are each independently an alkylene having 1-30 carbon atoms, wherein the alkylene group is linear, branched, cyclic, or combinations thereof. In certain of these embodiments, the alkylene can be straight chain or branched with 1-20 carbon atoms. In certain of these embodiments, the alkylene is of the formula $(CH_2)_n$, where n is an integer of 1 to 20.

In certain embodiments, $Y^1$, $Y^2$, and $Y^3$ each independently includes an arylene group (preferably, including up to 18 carbon atoms, up to 12 carbon atoms, or up to 6 carbon atoms), in addition to one or more alkylene groups and one or more heteroalkylene groups.

Exemplary Compounds

Exemplary Formula I structures include, but are not limited to, the following:

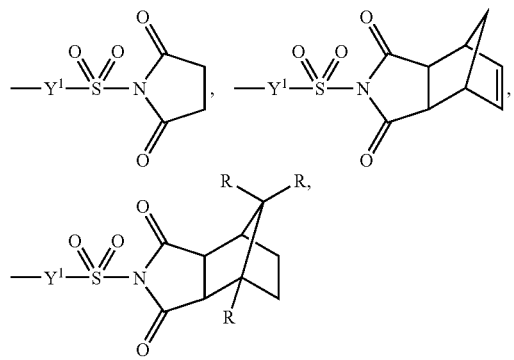

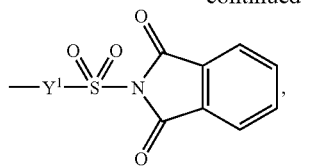

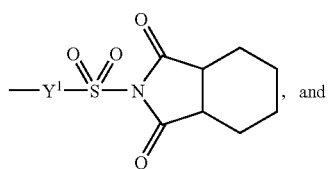

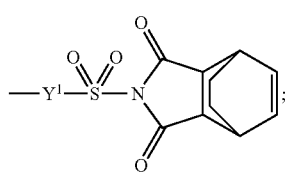

wherein: R is an alkyl; and $Y^1$ is the same as previously defined for Formula I. In certain of these exemplary embodiments, $Y^1$ can be —$Y^{1a}$—$Ar^1$— or —$Ar^1$—$Y^{1a}$—, wherein $Ar^1$ is an arylene (preferably, a phenylene), and $Y^{1a}$ is selected from the group consisting of a single bond, alkylene, heteroalkylene, carbonyl, carbonyloxy, carbonylimino, oxy, thio, —$NR^f$— where $R^f$ is hydrogen or alkyl, and combinations thereof. The functional groups of Formula I can be unsubstituted or substituted with a halo, alkyl, alkoxy, or combinations thereof.

Exemplary Formula I structures also include, but are not limited to, the following:

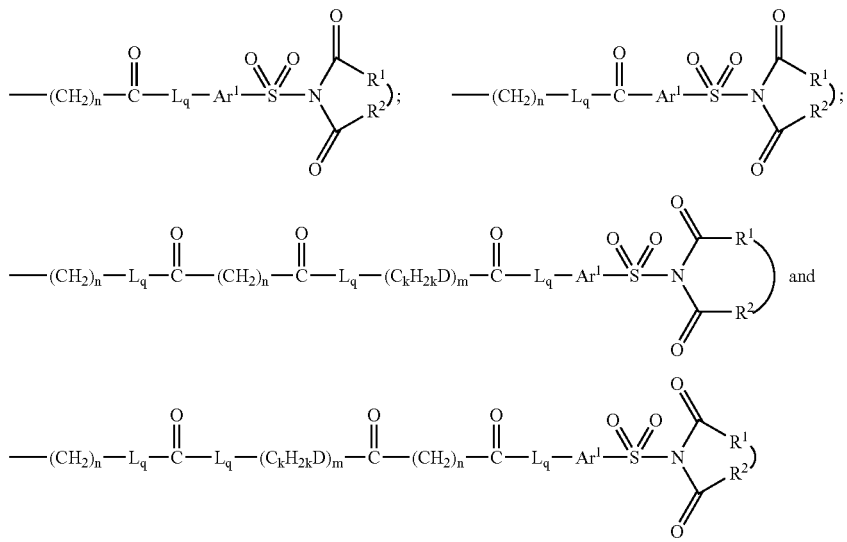

wherein: $R^1$ and $R^2$ are is the same as previously defined for Formula I; each n is independently an integer of 1 to 100; m is an integer of 1 to 200; k is an integer of 2 to 4; D is oxygen, sulfur, or NH; $Ar^1$ is an arylene group; each L is independently oxygen or $NR^f$ where $R^f$ is hydrogen or alkyl; and q is an integer of 0 or 1. In such embodiments, preferably, n is no greater than 80, no greater than 60, no greater than 40, no greater than 20, or no greater than 10; preferably, m is no greater than 150, no greater than 100, no greater than 80, no greater than 60, no greater than 40, no greater than 20, or no greater than 10; preferably, k is equal to 2; preferably, D is oxygen; and preferably, $Ar^1$ is phenylene.

Exemplary Formula II structures include, but are not limited to, the following:

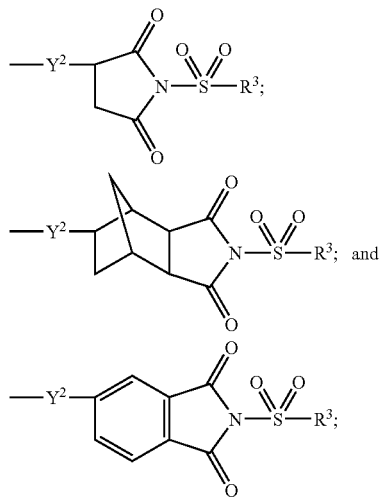

wherein $R^3$ and $Y^2$ are the same as previously defined for Formula II. The functional groups of Formula II can be unsubstituted or substituted with a halo, alkyl, alkoxy, or combinations thereof.

Exemplary Formula II structures also include, but are not limited to, the following:

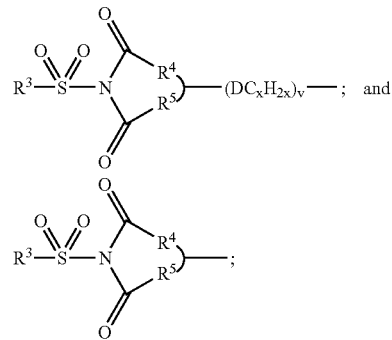

wherein: $R^3$, $R^4$, and $R^5$ are is the same as previously defined for Formula II; v is an integer of 1 to 200; x is an integer of 1 to 4; and D is oxygen, sulfur, or NH. In such embodiments, preferably, v is no greater than 150, no greater than 100, no greater than 80, no greater than 60, no greater than 40, no greater than 20, no greater than 10, no greater than 5, no greater than 4, no greater than 3, no greater than 2, or equal to 1, and more preferably, v is 1 or 2; preferably, x is no greater than 3, no greater than 2, or equal to 1, and more preferably, x is 1 or 2; and preferably, D is oxygen or sulfur.

An exemplary Formula III structure includes a heterocyclic group fused to an aromatic group as shown in the following formula:

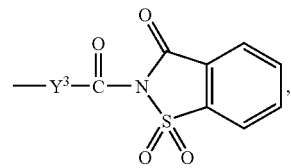

wherein $Y^3$ is the same as previously defined for Formula III.

In certain embodiments, the multifunctional compounds of the present invention include two or more pendant groups independently selected from the following formulas:

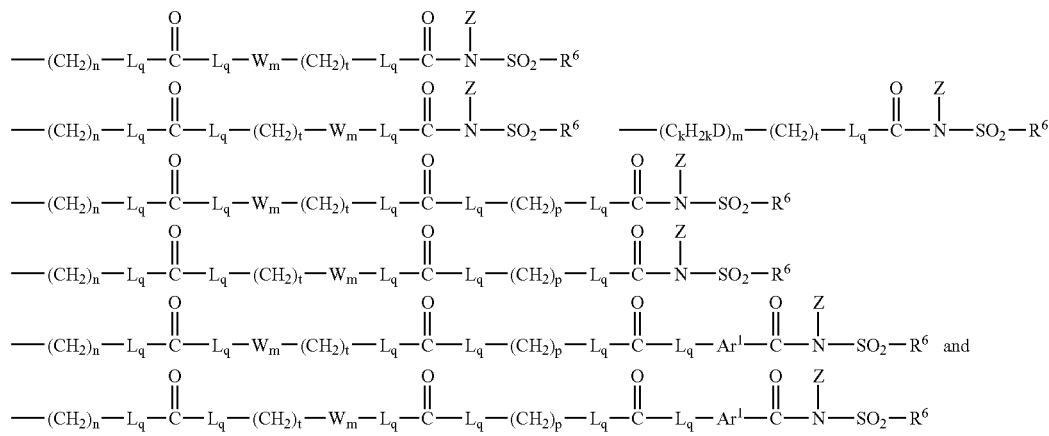

wherein: W is $C_kH_{2k}D$ or $DC_kH_{2k}$; D is oxygen, sulfur, or NH (preferably, oxygen); n is an integer of 1 to 100 (preferably no greater than 80, no greater than 60, no greater than 40, no greater than 20, no greater than 10); m is an integer of 1 to 200 (preferably no greater than 150, no greater than 100, no greater than 80, no greater than 60, no greater than 40, no greater than 20, no greater than 10); p is an integer of 1 to 10 (preferably no greater than 8, no greater than 6, no greater than 4, or no greater than 2); q is an integer of 0 or 1; t is an integer of 0 to 12 (preferably no greater than 10, no greater than 8, no greater than 6, no greater than 4, no greater than 2, or equal to 0); k is an integer of 2 to 4 (preferably no greater than 3, no greater than 2, or equal to 2); and each L is independently oxygen or $NR^f$ where $R^f$ is hydrogen or alkyl; with the proviso that at least one L is present in each $-L_q-C(O)-L_q-$ moiety and there are no heteroatom-heteroatom bonds.

In certain embodiments, the multifunctional compounds of the present invention include two or more pendant groups independently selected from the following formulas:

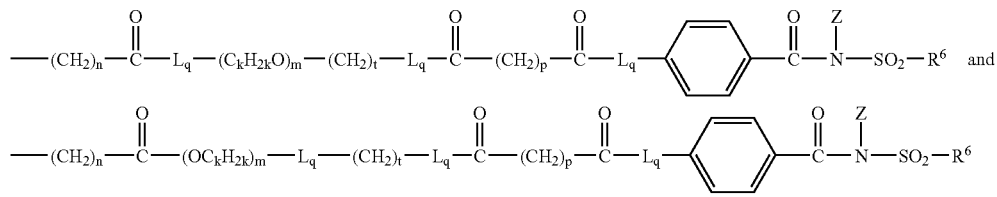

wherein: n is an integer of 1 to 100 (preferably no greater than 80, no greater than 60, no greater than 40, no greater than 20, no greater than 10); m is an integer of 1 to 200 (preferably no greater than 150, no greater than 100, no greater than 80, no greater than 60, no greater than 40, no greater than 20, no greater than 10); p is an integer of 1 to 10 (preferably no greater than 8, no greater than 6, no greater than 4, or no greater than 2); t is an integer of 0 to 12 (preferably no greater than 10, no greater than 8, no greater than 6, no greater than 4, no greater than 2, or equal to 0); k is an integer of 2 to 4 (preferably no greater than 3, no greater than 2, or equal to 2); each L is independently oxygen or $NR^f$ where $R^f$ is hydrogen or alkyl; and q is an integer of 0 or 1.

Preferred multifunctional compounds are difunctional or trifunctional compounds of the following formulas:

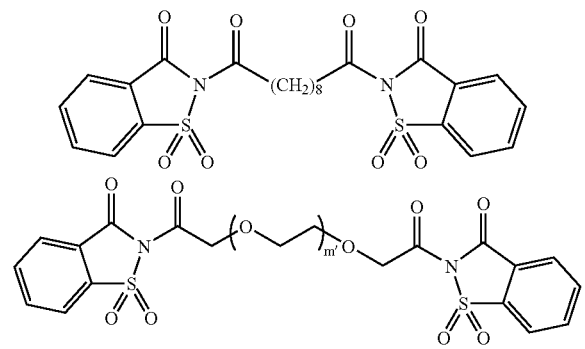

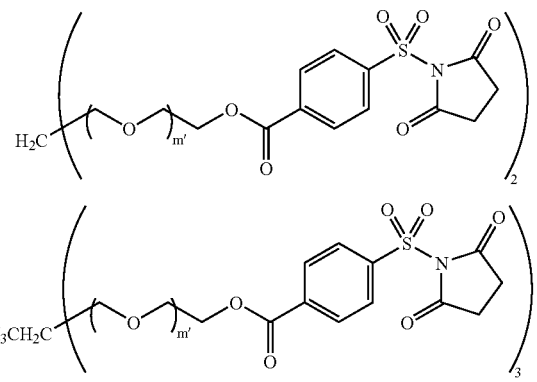

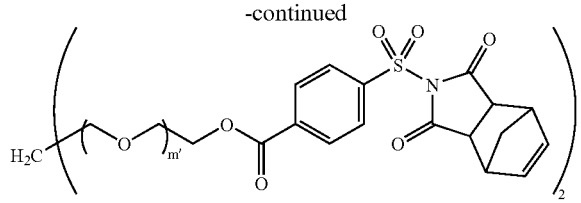

wherein m' is an integer of 1 to 200 (preferably no greater than 150, no greater than 100, no greater than 80, no greater than 60, no greater than 40, no greater than 20, no greater than 10).

Methods of Preparation

The functionally substituted amine capture agents of Applicants' Copending Pat. applications Ser. Nos. 10/714,053 and 10/713,174 filed on 14 Nov. 2003, and Ser. Nos. 10/987,075 and 10/987,522 filed on 12 Nov. 2004, can be used to make the multifunctional compounds of the present invention. This can be done by attaching such compounds to a core Q group bearing y complementary functional groups to give the multifunctional amine capture agents of the present invention. For example, $ClC(O)C_6H_4SO_2N(C(O)CH_2)_2$ (Preparative Example 2) can be reacted with a diol such as polyethylene glycol, or a triol such as trimethylolpropane ethoxylate. Also, a silane such as $(EtO)_3SiC_{10}H_{22}C(O)$-saccharin can be pre-reacted with tetraethoxysilane to form a sol-gel condensate including multiple amine capture acyl saccharin groups. Alternatively, the amine capture group can be formed at the terminus of a multifunctional Q group by the reactions illustrated in the Applicants' Copending Pat. applications Ser. Nos. 10/714,053 and 10/713,174 filed on 14 Nov. 2003, and Ser. Nos. 10/987,075 and 10/987,522 filed on 12 Nov. 2004.

For example, a Q group-containing multifunctional acid chloride can be reacted with sodium saccharin, or a Q group-containing multisulfonamide can be reacted with succinoyl chloride.

Uses

The multifunctional compounds of the invention can be used, for example, for immobilizing amine-containing material (e.g., the multifunctional compounds can be attached to a substrate with one functional group and at least one remaining functional group can react with an amine-containing material). In some embodiments, the amine-containing material is an amine-containing analyte. In other embodiments, the amine-containing materials are biomolecules such as, for example, amino acids, peptides, DNA, RNA, protein, enzymes, organelles, immunoglobins, or fragments thereof. The immobilized amine-containing materials can also be used for biological separations or for detection of the presence of various biomolecules. Additionally, the immobilized amine-containing materials can be used in bioreactors or as biocatalysts to prepare other materials. The substrate-attached multifunctional compound can be used to detect amine-containing analytes.

Biological amine-containing materials often can remain active after attachment to the substrate-attached multifunctional compound. For example, an immobilized antibody can bind with antigen or an immobilized antigen can bind to an antibody. An amine-containing material can bind to a bacterium. In a more specific example, the immobilized amine-containing material can bind to a *Staphylococcus aureus* bacterium (e.g., the immobilized amine-containing material can be a biomolecule that has a portion that can specifically bind to the bacterium).

The multifunctional compounds of the present invention can be attached to a wide variety of substrates, including metals, glasses, polymers, ceramics, etc. The substrates for this use typically have an amine group, which can be formed in wet chemistry techniques such as reacting a polyacrylate with an alkylenediamine under forcing conditions or a glass surface with an aminoalkylsilylating agent or by vapor techniques such as an ammonia plasma.

The compounds of the invention are particularly useful as crosslinkers to cause precipitation or gellation of amine-containing polymer. Such systems can be adhesives and are useful to bond or seal tissue in vivo, as described for naturally occurring polyamines in U.S. Pat. No. 5,583,114 and for synthetic polyamines in U.S. Pat. No. 5,874,500. These previously known systems utilized diesters of N-hydroxysuccinimide as the amine capture groups. The multifunctional compounds of the present invention typically have greater hydrolytic stability than acyl N-hydroxysuccinimides and consequently are more useful as gelling and tethering agents in aqueous systems.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

| Table of Abbreviations | |
|---|---|
| Abbreviation or Trade Designation | Description |
| EtOAc | Ethyl acetate |
| ACN | Acetonitrile |
| IPA | isopropyl alcohol |
| DMF | Dimethylformamide |
| PEG 3400 | Poly(ethylene glycol) $M_n$ about 3400 |
| PEG 1000 | Poly(ethylene glycol) $M_n$ approximately 1000; |
| PEG 600 | Poly(ethylene glycol)bis(carboxymethyl)ether) |
| diacid | $HO_2CCH_2(OC_2H_4)_nOCH_2COOH$ $M_n$ approximately 600 commercially available from Fluka Holding AG, Buchs, Switzerland |
| NMP | N-methylpyrrolidinone |
| TEA | Triethylamine |
| TPEG 990 | A glycerin-started trifunctional polyethylene glycol $M_n$ approximately 990 commercially available from Dow Chemical Company, Midland, MI |
| THF | Tetrahydrofuran |
| Na saccharin | Sodium salt of saccharin, dehydrated |

Preparative Example 1

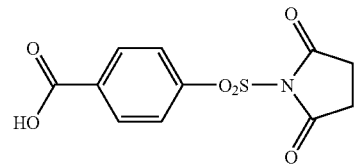

In a glass reaction vessel, a mixture of DMF (154 milliliters), 4-carboxybenzenesulfonamide (30.0 grams), succinic anhydride (16.41 grams), and triethylamine (33.19 grams) was stirred and heated to 50° C. under a nitrogen atmosphere for four hours. The mixture was allowed to cool to room temperature, acetic anhydride (18.27 milliliters) was added and the mixture was stirred at room temperature for an additional three hours. The mixture was poured into 400 milliliters of stirred 1N aqueous HCl. This mixture was filtered, washed with deionized water and dried in a vacuum oven to afford the desired product. Yield: 36.94 grams.

Preparative Example 2

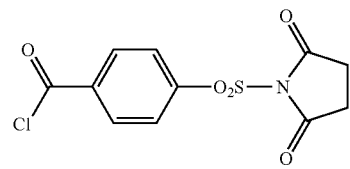

In a glass reaction vessel containing a stirred mixture of the carboxy-containing product of Preparative Example 1 (20.0 grams) and dry acetonitrile (85 grams) was added thionyl chloride (10.0 grams) and DMF (1 drop). The resulting mixture was stirred and heated under reflux for one hour, cooled to room temperature and further cooled in an ice bath, which resulted in the formation of a solid precipitate. The solid was collected by filtration, washed sequentially with cold acetonitrile and cold toluene, and dried overnight in a vacuum oven at 50° C. to give the desired product. Yield: 17.7 grams.

Preparative Example 3

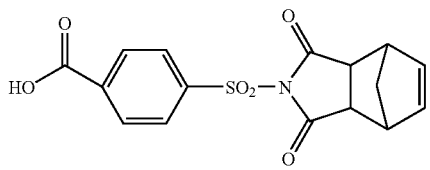

In a glass reaction vessel, a mixture of norbornene-2,3-dicarboxylic anhydride (26.9 grams), 4-carboxybenzene-sulfonamide (30.0 grams), TEA (49.8 grams) and DMF (82 grams) were stirred and heated to 50° C. under a nitrogen atmosphere for two hours followed by heating overnight at 90° C. The mixture was cooled to room temperature and acetic anhydride (18.3 grams) was added to the flask. The mixture was stirred overnight at room temperature, poured into aqueous 1NHCl and the resultant solid was isolated by filtration and dried using a vacuum oven. The resulting solid was recrystallized from glacial acetic acid to give the desired product. Yield: 12.6 grams.

Preparative Example 4

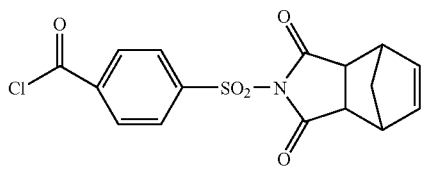

In a glass reaction vessel fitted with a reflux condenser and a nitrogen inlet, a mixture of the carboxylic acid product of Preparative Example 3 (5.0 grams), thionyl chloride (2.2 grams), DMF (1 drop) and ACN (28.9 milliliters) were stirred under a nitrogen atmosphere and heated to reflux for one hour. The mixture was allowed to cool to room temperature and the volatile components were removed using a rotary evaporator. The resultant solid was washed into a fritted glass funnel, washed with diethyl ether, and then dried at room temperature under a stream of nitrogen gas to afford the desired product. Yield: 4.7 grams.

Example 1

Preparation of

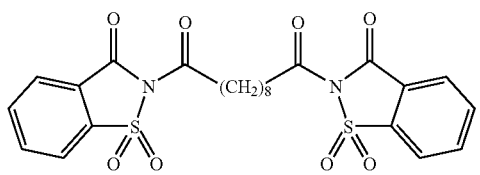

Sebacoyl chloride (6.0 grams, 0.025 mol) was added to a stirred slurry of dry Na saccharin (10.25 grams, 0.50 mol) and 200 milliliters of acetone under a nitrogen atmosphere. The resulting mixture was stirred for 20 hours at room temperature. IR spectroscopy showed the absence of peaks for the group —C(O)Cl. The mixture was filtered and washed with acetone to give 11.8 grams of white solid. The acetone was removed from the wash solution to yield 3.7 grams of a tan solid that was combined with the filtrate, washed with water and dried to give the desired product (structure confirmed by NMR) which was slightly soluble in ACN, acetone and 2-butanone. Yield: 9.1 grams.

Example 2

Preparation of

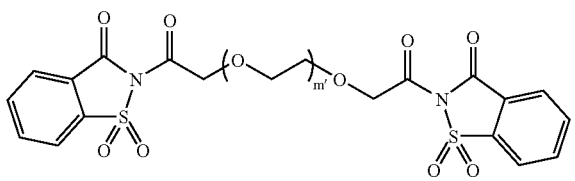

Ten milliliters of $SOCl_2$ was added to a mixture of PEG 600 diacid (30 grams, 0.05 mol, where m' is approximately 14) in 100 milliliters $CH_2Cl_2$ with immediate evolution of HCl. After 20 hours, the solvent was removed under vacuum to give 33.6 grams of pale yellow oil. Of this, 6.4 grams (0.01 mol) was added to dry Na saccharin (4.1 grams, 0.02 mol). The resulting slurry was stirred for 24 hours, filtered and dried under vacuum to give the desired product as a pale tan syrup. Yield: 9.3 grams.

Example 3

Preparation of

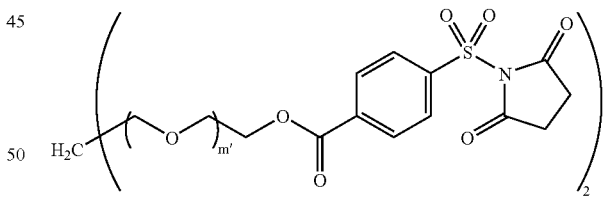

In a glass reaction vessel, a sample of the chlorocarbonyl product of Preparative Example 2 (1.0 grams) was dissolved in NMP (3.6 grams) and chilled in an ice bath. A solution of PEG 3400 (3.54 grams, where m' is approximately 77) in THF (3.54 grams) was slowly added to the flask. The mixture was stirred overnight as the mixture warmed to room temperature. The mixture was concentrated, recrystallized with IPA. The resulting white solid was filtered and rinsed with chilled IPA to give the desired product. Yield: 4.17 grams. A hydrogel was formed by the addition of polyethylenimine, average $M_w$ approximately 2,000, 50 wt. % solution in water (0.17 grams) to an aqueous solution of this product (0.50 grams), at 50 weight percent.

Example 4

Preparation of

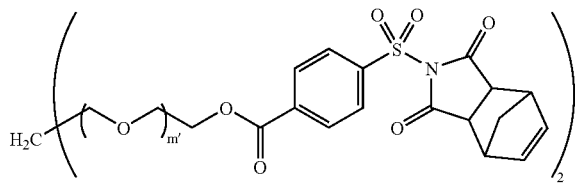

In a glass reaction vessel, a sample of the chlorocarbonyl product of Preparative Example 4 (1.99 grams) was dissolved in THF (10 grams). A solution of PEG 3400 (8.20 grams, where m' is approximately 77), pyridine (0.48 grams), and THF (3.54 grams) were slowly added and the resulting mixture was stirred overnight. The mixture was concentrated and recrystallized with IPA. The resulting white solid was filtered and rinsed with chilled IPA to give the desired product. Yield: 9.0 grams.

Example 5

Preparation of

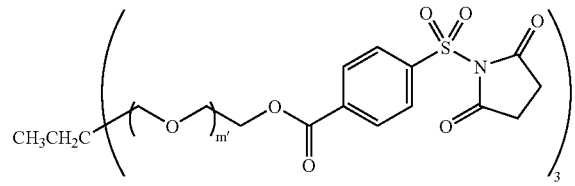

In a glass reaction vessel, a sample of the chlorocarbonyl product of Preparative Example 2 (2.00 grams) was dissolved in THF (8 grams). A solution of TPEG 990 (2.07 grams, where m' is approxiamtely 22), TEA (0.70 grams), and TBF (8.0 grams) were slowly added and the resulting mixture was stirred overnight. IR spectroscopy showed the absence of peaks for the group —C(O)Cl. The mixture was concentrated, reconstituted in EtOAc, and filtered to give a clear, colorless solution at 24.5% solids.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the formula:

wherein each A is independently selected from a functional group of Formula (III):

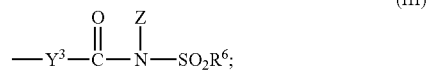

wherein:
each $R^6$ is independently an alkyl, fluoroalkyl, chloroalkyl, aryl, —$NR^cR^d$ wherein $R^c$ and $R^d$ are each an alkyl group or taken together with the nitrogen atom to which they are attached form a four to eight membered cyclic group, or $R^6$ taken together with $R^e$ and the groups to which they are attached form the four to eight membered heterocyclic or heterobicyclic group that can be fused to the optional aromatic group, optional saturated or unsaturated cyclic group, or optional saturated or unsaturated bicyclic group;

each Z is independently an alkyl, aryl, or —$(CO)R^e$ wherein $R^e$ together with $R^6$ and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group;

each $Y^3$ is independently a single bond or a divalent group selected from the group consisting of an alkylene, heteroalkylene, arylene, heteroarylene, carbonyl, carbonyloxy, carbonylimino, oxy, thio, —$NR^f$— where $R^f$ is hydrogen or alkyl, and combinations thereof;

Q is a single bond or an y-valent atom or group; and
y is an integer of 2 to 10;
with the proviso that Q, and $Y^3$ are free of disulfide groups.

2. The compound of claim 1 wherein each $Y^3$ is independently selected from the group consisting of groups having the following formulas: —$Y^{1a}$—$Ar^1$— and —$Ar^1$—$Y^{1a}$—, wherein:
$Ar^1$ is an arylene; and
$Y^{1a}$ is selected from the group consisting of a single bond, alkylene, heteroalkylene, carbonyl, carbonyloxy, carbonylimino, oxy, thio, —$NR^f$— where $R^f$ is hydrogen or alkyl, and combinations thereof.

3. The compound of claim 1 wherein each $Y^3$ each independently comprises a first alkylene group linked to an arylene group with a group selected from the group consisting of a carbonyl, carbonyloxy, carbonylimino, oxy, thio, —$NR^f$— where $R^f$ is hydrogen or alkyl, and combinations thereof.

4. The compound of claim 1 wherein each $Y^3$ independently comprises a first heteroalkylene group linked to an arylene with a group selected from the group consisting of a carbonyl, carbonyloxy, carbonylimino, oxy, thio, —$NR^f$— where $R^f$ is hydrogen or alkyl, and combinations thereof.

5. The compound of claim 1 wherein each $Y^3$ independently comprises a first alkylene group connected to a second alkylene group or to a first heteroalkylene group with a group selected from the group consisting of a carbonyl, carbonylimino, carbonyloxy, oxy, thio, —$NR^f$— where $R^f$ is hydrogen or alkyl, and combinations thereof.

6. The compound of claim 1 wherein each $Y^3$ is independently a heteroalkylene group.

7. The compound of claim 1 wherein each $Y^3$ independently comprises a first heteroalkylene group connected to a second heteroalkylene group or to a first alkylene group with a group selected from the group consisting of a carbonyl, carbonylimino, carbonyloxy, oxy, thio, —$NR^f$— where $R^f$ is hydrogen or alkyl, and combinations thereof.

8. The compound of claim 1 wherein each $Y^3$ is independently a heteroalkylene having 1-30 carbon atoms and up to 30 heteroatoms selected from the group consisting of N, O, S, and combinations thereof, wherein the heteroalkylene group is linear, branched, cyclic, or combinations thereof.

9. The compound of claim 1 wherein each $Y^3$ is independently an alkylene having 1-30 carbon atoms, wherein the alkylene group is linear, branched, cyclic, or combinations thereof.

10. The compound of claim 1 wherein each $Y^3$ independently comprises an arylene group, in addition to one or more alkylene groups and one or more heteroalkylene groups.

11. The compound of claim 1 wherein each A is independently selected from the group consisting of functional groups having the following formulas:

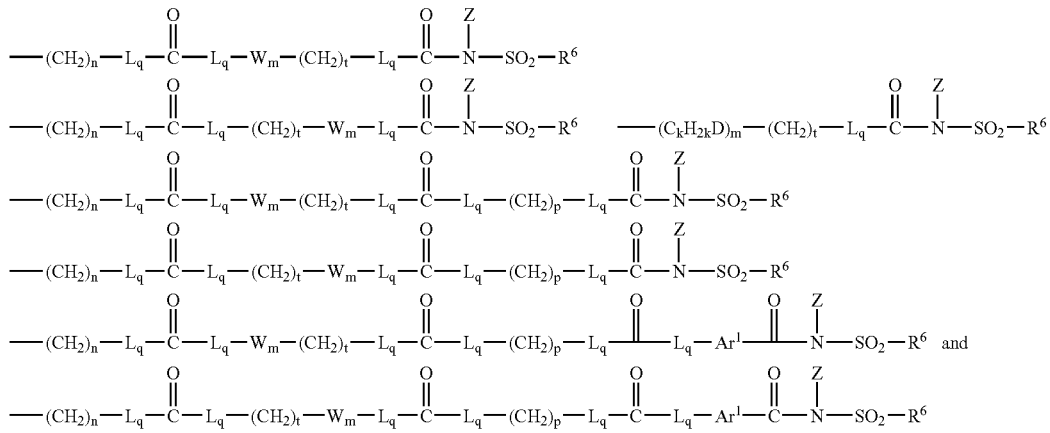

wherein:
W is $C_kH_{2k}D$ or $DC_kH_{2k}$;
D is oxygen, sulfur, or NH;
n is an integer of 1 to 100;
m is an integer of 1 to 200;
p is an integer of 1 to 10;
q is an integer of 0 or 1;
t is an integer of 0 to 12;
k is an integer of 2 to 4; and
each L is independently oxygen or $NR^f$ where $R^f$ is hydrogen or alkyl;
with the proviso that at least one L is present in each $-L_q-C(O)-L_q-$ moiety and there are no heteroatom-heteroatom bonds.

12. The compound of claim 1 wherein each A is independently selected from the group consisting of functional groups having the following formulas:

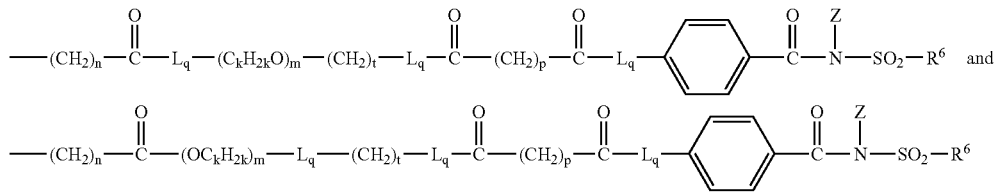

wherein:
n is an integer of 1 to 100;
m is an integer of 1 to 200;
p is an integer of 1 to 10;
q is an integer of 0 or 1;
t is an integer of 0 to 12;
k is an integer of 2 to 4; and
each L is independently oxygen or $NR^f$ where $R^f$ is hydrogen or alkyl.

13. The compound of claim 1 wherein Z is an alkyl or aryl group.

14. The compound of claim 1 wherein Z is a $-(CO)R^e$ group that together with $R^6$ and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group.

15. The compound of claim 1 wherein each A group has the following formula:

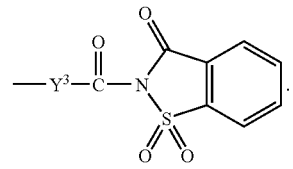

16. The compound of claim 1 wherein $R^6$ is a $C_{1-30}$ alkyl.

17. The compound of claim 1 wherein Q is an atom selected from C, N, S, O, or P, or is a y-valent group containing up to 20 carbon atoms and up to 6 heteroatoms and/or functional groups.

18. The compound of claim 1 wherein y is 2 or 3.

* * * * *

UNITED STATES PATENT AND TRADEMARK OFFICE
CERTIFICATE OF CORRECTION

| | | |
|---|---|---|
| PATENT NO. | : 7,402,678 B2 | Page 1 of 1 |
| APPLICATION NO. | : 11/015543 | |
| DATED | : July 22, 2008 | |
| INVENTOR(S) | : Karl E. Benson | |

It is certified that error appears in the above-identified patent and that said Letters Patent is hereby corrected as shown below:

On the Title Pg, Item (56) (U.S. Patent Documents), Line 12 - Delete "Bickoff et al." and insert -- Clark et al. --, therefor.

Column 3, Line 15 - Delete "—(CO)—." and insert -- —(CO)O—. --, therefor.

Column 3, Line 60 - Delete "(A)y-Q" and insert -- (A-)y-Q --, therefor.

Column 5, Line 28 - Delete "R1" and insert -- Ra --, therefor.

Column 9, Line 1 - after "$R^2$ are" delete "is".

Column 10, Line 18 (Approx.) - Delete "$R^{3,}$ $R^{4,}$" and insert -- $R^3$, $R^4$, --, therefor.

Column 14, Line 14 (Approx.) - after "Poly" insert -- ( --.

Column 15, Line 24 (Approx.) - Delete "1NHCl" and insert -- 1 N HCl --, therefor.

Column 17, Line 36 - Delete "approxiamtely" and insert -- approximately --, therefor.

Column 17, Line 36 - Delete "TBF" and insert -- THF --, therefor.

Column 18, Claim 3, Lines 1-2 after "wherein each $Y^3$" delete "each".

Column 19, Line 30 - In Claim 11, delete "NII;" and insert -- NH; --, therefor.

Signed and Sealed this

Tenth Day of November, 2009

David J. Kappos
*Director of the United States Patent and Trademark Office*